United States Patent
Wilcox et al.

(10) Patent No.: US 10,617,387 B2
(45) Date of Patent: Apr. 14, 2020

(54) ARRAY SONOGRAPHY FOR ESOPHAGEAL CHARACTERIZATION

(71) Applicant: RefloDx, LLC, Clearfield, UT (US)

(72) Inventors: Andrew Wilcox, Layton, UT (US); Samuel Thomas, Salt Lake City, UT (US); Joshua Jones, Cottonwood Heights, UT (US); Timothy Pickett, Highland, UT (US)

(73) Assignee: Reflodx, LLC, Clearfield, UT (US)

( * ) Notice: Subject to any disclaimer, the term of this patent is extended or adjusted under 35 U.S.C. 154(b) by 231 days.

(21) Appl. No.: 15/689,874

(22) Filed: Aug. 29, 2017

(65) Prior Publication Data
US 2018/0055482 A1    Mar. 1, 2018

Related U.S. Application Data (60) Provisional application No. 62/382,738, filed on Sep. 1, 2016.

(51) Int. Cl.
*A61B 8/00* (2006.01)
*A61B 8/08* (2006.01)
(Continued)

(52) U.S. Cl.
CPC .............. *A61B 8/4427* (2013.01); *A61B 8/08* (2013.01); *A61B 8/145* (2013.01); *A61B 8/15* (2013.01); *A61B 8/4236* (2013.01); *A61B 8/4477* (2013.01); *A61B 8/5223* (2013.01); *A61B 8/56* (2013.01)

(58) Field of Classification Search
CPC .. A61B 8/08; A61B 8/145; A61B 8/15; A61B 8/4236; A61B 8/4427; A61B 8/4477; A61B 8/5223; A61B 8/56
See application file for complete search history.

(56) References Cited

U.S. PATENT DOCUMENTS

| | | |
|---|---|---|
| 5,247,938 A | 9/1993 | Silverstein et al. |
| 5,479,935 A | 1/1996 | Essen-Moller |

(Continued)

FOREIGN PATENT DOCUMENTS

| | | | | |
|---|---|---|---|---|
| WO | WO2011127211 | * | 10/2011 | ............. A61B 5/042 |
| WO | WO 2012/123918 A1 | | 9/2012 | |
| WO | WO2012123918 | * | 9/2012 | ............... A61B 8/08 |

OTHER PUBLICATIONS

Gabay (Charge and Battery Control Sensors and Solutions, Digikey.com, Digi-Key Electronics, https://www.Digikey.com/en/articles/techzone/2016/may/charge-and-battery-control-sensors-and-solutions; May 2016. (Year: 2016) (Year: 2016).*

(Continued)

*Primary Examiner* — Pascal M Bui Pho
*Assistant Examiner* — Alexei Bykhovski
(74) *Attorney, Agent, or Firm* — Durham Jones & Pinegar; Sarah W. Matthews (57) ABSTRACT

The present invention relates to devices for detecting esophageal state changes. More specifically, the present invention relates to a lightweight, portable, user-operable device capable of detecting gastroesophageal reflux events. The sonography array can also be used to track the frequency of gastroesophageal reflux events, and can either store or deliver the data either to a practitioner's server or to a user's electronic device.

18 Claims, 8 Drawing Sheets

(51) Int. Cl.
*A61B 8/14* (2006.01)
*A61B 8/15* (2006.01)

(56) References Cited

U.S. PATENT DOCUMENTS

| | | | |
|---|---|---|---|
| 5,833,625 | A | 11/1998 | Essen-Moller |
| 6,478,744 | B2 | 11/2002 | Mohler |
| 6,551,252 | B2 | 4/2003 | Sackner et al. |
| 7,604,598 | B2 | 10/2009 | Rein et al. |
| 8,568,336 | B2 | 10/2013 | Gewolb et al. |
| 8,706,208 | B2 | 4/2014 | Chiao et al. |
| 9,002,427 | B2 | 4/2015 | Tupin, Jr. et al. |
| 2005/0027679 | A1 | 2/2005 | Sample |
| 2008/0004547 | A1 | 1/2008 | Dinsmoor et al. |
| 2008/0027679 | A1 | 1/2008 | Sfiklarski |
| 2008/0306355 | A1* | 12/2008 | Walker .................. A61B 5/42 600/301 |
| 2010/0022883 | A1* | 1/2010 | Satoh .................... A61B 8/14 600/447 |
| 2011/0060225 | A1* | 3/2011 | Cogan ................. B06B 1/0207 600/459 |
| 2011/0282249 | A1 | 11/2011 | Tsoref et al. |
| 2014/0073883 | A1 | 3/2014 | Rao et al. |
| 2016/0013394 | A1 | 1/2016 | Savoia et al. |

OTHER PUBLICATIONS

International Search Report and Written Opinion of the International Searching Authority from related PCT Appl. PCT/US2017/049150, dated Nov. 20, 2017.

\* cited by examiner

ARRAY SONOGRAPHY FOR ESOPHAGEAL CHARACTERIZATION

BACKGROUND

State of the Art

The present invention relates to devices for characterizing the state of the esophagus which allows for detecting Gastroesophageal reflux, swallow events, etc. More specifically, the present invention relates to a lightweight, portable, user-operable device capable of detecting Gastroesophageal reflux (GER) events. The sonography array can also be used to track the frequency of Gastroesophageal reflux events, and can either store or deliver the data either to a practitioner's server or to a user's electronic device.

Field of Art

Gastroesophageal reflux is a common medical problem across the world. Heartburn, also called acid indigestion or acid reflux, is the most common symptom of GER events. Occasional acid reflux may cause nausea, coughing, or a sharp pain in the chest, symptoms which are sometimes mistaken for more serious problems such as a heart attack or an embolism. Chronic acid reflux, however, can damage the mucosal lining of the esophagus, eventually resulting in injuries such as esophageal strictures, Barrett's esophagus metaplasia, granulomas in the lungs (when there is a retrograde flow of gastric contents to the upper aero-digestive tract) and even cancers. This damage can accumulate silently, or with only mild symptoms, over the course of years.

Thus, determining whether a patient is truly experiencing gastroesophageal reflux, and how often, is of great importance in preventative care. Because gastroesophageal reflux is rarely a constant condition—that is, acid may enter the esophagus under particular conditions or at particular times, but not others—an in-office swab is not effective to diagnose the problem. Various means of continuous monitoring over several days are used, such as esophageal pH monitoring, in which a probe with radio transmitter is inserted nasally and worn for several days. The end of the catheter may be taped at the nostrils to hold the probe at the correct depth. The probe may be coated with viscous lidocaine to reduce severe chest pain, which occurs in around 5% of patients. Occasionally, the probe may dislodge prematurely from the preferred placement and enter the stomach. Additionally, children and some adults often cannot tolerate the irritation of wearing the probe and catheter.

Another technique is Multiple Intraluminal Impedance (MII). One of the hallmarks of gastroesophageal reflux is that small amounts of air or fluid escape the stomach and irritate the esophagus. This bolus of air or fluid has a different electrical impedance, compared with the surrounding esophageal tissue or a bite of swallowed food. Refluxate, or stomach liquid, has a lower impedance than esophageal lining, while air has higher impedance. In order to detect this bolus, however, clinicians have needed to insert a catheter and probe—often steel rings separated by an isolator—which suffers from the same drawbacks as the pH probe outlined above, and there is no improvement of patient comfort while wearing the device.

The bolus of air or stomach contents indicative of gastroesophageal reflux, however, can be detected non-invasively—for example, by transabdominal ultrasound, which is performed at around 5 MHz. A bolus of air or liquid reflects these waves differently than surrounding esophageal tissue, and thus can be tracked. These monitoring devices are comfortable to use, but are subject to many drawbacks. The equipment for a transabdominal ultrasound is bulky, expensive, and cannot be taken with the patient or worn during daily activities. An experienced practitioner is required in order to correctly position the ultrasound wand and interpret the image. As a result, typically monitoring is done for only about 15 minutes.

Currently there is no device available for the detection of gastroesophageal reflux that can be worn by as an ambulatory device over the course of several days, is comfortable to wear, is simple enough that a caregiver may set up the device and instruct a patient during a routine office visit, and does not interfere with the performance of daily activities. Thus there is a need for a device which not only performs one or more of these functions for a variety of body sizes and ages of people, but is also capable of taking frequent samples, distinguishing false positives from actual reflux events, and sending or storing the data generated.

It is further advantageous if the device is capable of correlating acoustic events (such as speech, coughs, burps, hiccups, etc.) with the data of reflux events. Additionally, it is advantageous if the device continues to function when dropped or tugged on, withstands a physiological range of temperature and humidity, contains sufficient battery power to operate continuously for a period of time greater than 24 hours, and has a means to provide feedback to the user and offline analysis by a clinician.

SUMMARY OF THE INVENTION

The following summary of the present invention is not intended to describe each illustrated embodiment or every possible implementation of the invention, but rather to give illustrative examples of application of principles of the invention.

In some embodiments, the sonography array for esophageal characterization includes an ambulatory data collection box with output indicators, the output indicators including sensor status indicators and utility indicators; electrical leads which may be detachably attached to the data collection box (or the data collection box may be wirelessly connected), and a sensor pad attached to the leads. In other configurations, the data collection box and the sensors may be wirelessly connected. In some embodiments, the sensors may include an array of at least two sensors, such as a grid or a strip of sensors.

In other embodiments, the sonography array for esophageal characterization also includes a speaker or other means of producing sound. In addition, the sonography array may include a microphone for detecting audible sounds.

In still other embodiments, the sensors of the sonography array for esophageal characterization may be piezoelectric transducers, which may emit sound waves in a range between 100 kHz and 10 MHz.

In some embodiments, the sensors of the sonography array for esophageal characterization may have a variable sampling frequency of 0.1 Hz to 100 Hz.

In still other embodiments, the data collection box may be adapted to alter the sampling frequency of all of the sensors simultaneously.

In still other embodiments, the data collection box may be adapted to determine which sensors produce a poor noise to signal ratio, and may adjust the sampling frequency of just a few sensors rather than the entire grid, array, or strip of sensors.

In still other embodiments, the data collection box may also include a battery, a power and ground sensor, a voltage regulator, and a digital processor or microprocessor.

In some embodiments, the battery of the data collection box may be adapted to power the sensors to enable them to perform normal recording functions for greater than 24 hours.

In other embodiments, a software interface may be included, capable of presenting data from the sensors to a user at varying levels of granularity. In some embodiments, this granularity may be determined by a real time flag placed on the data, or by distance—e.g. the distance that a reflux event travels up the esophagus.

In still other embodiments, one method of detecting esophageal state may include: providing a data collection box, providing a sensor array comprising one or more sensors, connecting the sensor array to the data collection box; calibrating the sensor array, selectively identifying the sensors positioned to detect esophageal state; and recording data generated by the sensors positioned to characterize the esophageal state.

In some embodiments, one method of detecting gastroesophageal reflux may include: providing an ancillary sensor, detecting esophageal events which are not gastroesophageal reflux, and modulating the behavior of the sensors during esophageal events which are not gastroesophageal reflux.

In some methods of use, the data collection box may include sensor indicators, utility indicators, analog to digital converters, digital to analog converters, driving circuitry, switching circuitry, signal amplification, filtering and processing circuitry, a digital signal processor, charging circuitry, an external direct current connector, a USB connector, a real time clock, and voltage regulators.

In some embodiments, one method of detecting gastroesophageal reflux may include flagging data generated by the sensors positioned to detect gastroesophageal reflux with a real time stamp or metadata, and providing a graph of data generated by the sensors positioned to detect gastroesophageal reflux with a real time stamp.

These and other aspects of the present invention are realized in a sonography array for esophageal characterization as shown and described in the following figures and related description. It will be appreciated that various embodiments of the invention may not include each aspect set forth above and aspects discussed above shall not be read into the claims unless specifically described therein.

BRIEF DESCRIPTION OF THE DRAWINGS

Various configurations of the present disclosure are shown and described in reference to the numbered drawings, wherein.

It will be appreciated that the drawings are illustrative and not limiting of the scope of the invention which is defined by the appended claims. The embodiments shown accomplish various aspects and objects of the invention, however it will be appreciated that the claims are to be interpreted based on the language therein and not the various aspects and objects which may or may not be achieved. It will be appreciated that it is not possible to clearly show each element and aspect of the present disclosure in a single figure, and as such, multiple figures are presented to separately illustrate the various details of different aspects of the invention in greater clarity. Similarly, not all configurations or embodiments described herein or covered by the appended claims will include all of the aspects of the present disclosure as discussed above. Additionally, not every embodiment need accomplish all advantages of the present invention.

DETAILED DESCRIPTION

Various aspects of the invention and accompanying drawings will now be discussed in reference to the numerals provided herein so as to enable one skilled in the art to practice the present invention. The skilled artisan will understand, however, that the methods described below can be practiced without employing these specific details, or that they can be used for purposes other than those described herein. Indeed, they can be modified and can be used in conjunction with products and techniques known to those of skill in the art in light of the present disclosure. The drawings and the descriptions thereof are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

Reference in the specification to "one configuration," "one embodiment" "one aspect" or "a configuration," "an embodiment" or "an aspect" means that a particular feature, structure, or characteristic described in connection with the configuration may be included in at least one configuration and not that any particular configuration is required to have a particular feature, structure or characteristic described herein.

The appearances of the phrase "in one configuration" or similar phrases in various places in the specification are not necessarily all referring to the same configuration, and may not necessarily limit the inclusion of a particular element of the invention to a single configuration, rather the element may be included in other or all configurations discussed herein. Thus it will be appreciated that the claims are not intended to be limited by the representative configurations shown herein. Rather, the various representative configurations are simply provided to help one of ordinary skill in the art to practice the inventive concepts claimed herein.

Furthermore, the described features, structures, or characteristics of embodiments of the present disclosure may be combined in any suitable manner in one or more embodiments. In the following description, numerous specific details may be provided, such as examples of products or manufacturing techniques that may be used, to provide a thorough understanding of embodiments of the invention. One skilled in the relevant art will recognize, however, that embodiments discussed in the disclosure may be practiced without one or more of the specific details, or with other methods, components, materials, and so forth. In other instances, well-known structures, materials, or operations may not be shown or described in detail to avoid obscuring aspects of the invention.

Before the present invention is disclosed and described in detail, it should be understood that the present invention is not limited to any particular structures, process steps, or materials discussed or disclosed herein. More specifically, the invention is defined by the terms set forth in the claims. It should also be understood that terminology contained herein is used for the purpose of describing particular aspects of the invention only and is not intended to limit the invention to the aspects or embodiments shown unless expressly indicated as such. Likewise, the discussion of any particular aspect of the invention is not to be understood as a requirement that such aspect is required to be present apart from an express inclusion of that aspect in the claims.

It should also be noted that, as used in this specification and the appended claims, singular forms such as "a," "an," and "the" may include the plural unless the context clearly dictates otherwise. Thus, for example, reference to "a bracket" may include an embodiment having one or more of such brackets, and reference to "the transducer" may include reference to one or more of such transducers.

As used herein, the term "substantially" refers to the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that 'a circuit substantially enclosed in a pad' would be substantially surrounded, even if the pad included a slit or channel formed along a portion thereof. The use of "substantially" is equally applicable when used in a negative connotation to refer to the complete or near complete lack of an action, characteristic, property, state, structure, item, or result.

As used herein, the term "about" is used to provide flexibility to a numerical range endpoint by providing that a given value may be "a little above" or "a little below" the endpoint while still accomplishing the function associated with the range.

As used herein, a plurality of items, structural elements, compositional elements, and/or materials may be presented in a common list for convenience. However, these lists should be construed as though each member of the list is individually identified as a separate and unique member.

Concentrations, amounts, proportions and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

The invention and accompanying drawings will now be discussed in reference to the numerals provided therein so as to enable one skilled in the art to practice the present invention. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

Figure 1:
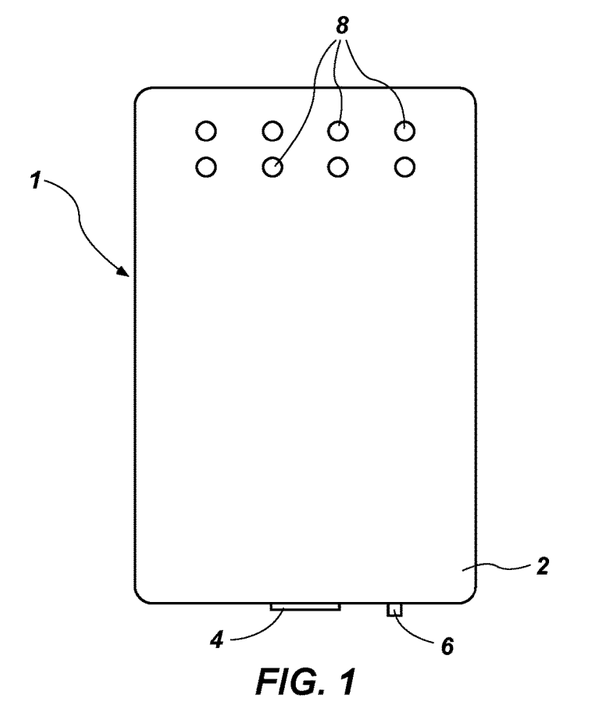
FIG. 1 shows a top view of one embodiment of a data collection box.

Turning now to FIG. 1, there is shown a top view of one embodiment of an electronic packaging box, indicated generally at 1. The shape of the box may be approximately rectangular, or may be circular, or may be incorporated into a belt or other wearable object. In the embodiment shown in the figure, the box 1 may measure, for example, approximately 3 inches by 4.5 or 5 inches, with a thickness of less than approximately 0.5 inches. The corners 2 of the box 1 may be substantially rounded, in order to make the box more comfortable to grip or to wear. The box 1 may further include a USB or connectivity port 4, a power button 6, and one or more indicator lights 8.

It may be advantageous if the electronics housing 1 is adapted to protect the contents from sustained high humidity and temperatures and fluid or particle ingress, because the box 1 may be worn close to a body for several days and under varying physiological conditions. Indeed, because gastroesophageal reflux may occur only under stressful conditions, such as during exertion at high temperatures, it may be advantageous if the box or housing 1 is protected against moisture infiltration. Means of sealing the electronic housing 1 may include, for example, sealing locknuts, limited enclosure penetrations, ensuring that the USB port 4 or other penetrations are located at a lower point when the device is worn as intended, and encasing components in electrical tape, insulating potting compounds, and/or butyl self-adhesive rubber tape. Alternately or in addition, the enclosure may be insulated.

It is advantageous if the box 1 is formed of a durable and shock-resistant material, for example, plastic or silicone. It is advantageous if the electronics housing 1 passes a 5-foot drop test. It is also advantageous if the surface can be finished or colored.

In some embodiments, the power button 6 may be recessed such that it is accessible by an adult's thumbnail or a pen or other pointed object, but cannot be accidentally bumped or accessed by a child.

It is advantageous if the box 1 is reusable, in order to reduce costs incurred by patients. In order to facilitate use, the box 1 may be equipped with a belt clip, hook and loop fastener, or other means of securing a small electronic device to a user.

In some embodiments in which sensors are attached to the electronics housing 1 on multiple leads (discussed below, see also FIG. 7) the box 1 may include more than one indicator lights 8, including an indicator light 8 for each sensor adapted to display information such as whether a particular sensor has made good contact, whether the sensor is positioned properly, the sensor's recording status, whether the sensor is detecting possible reflux, whether the sensor is powered, and the like. These modes may be cycled through using a cycling button (not shown.) Additionally, the lights 8 may be arrayed in pairs. This is particularly useful when some sensors should be placed against the chest, and some against the corresponding location on the user's back. The paired lights arrangement may thus be used to indicate whether a given pair of sensors are placed and synchronized properly.

An additional indicator light 8 may be provided to display battery life.

Figure 2:
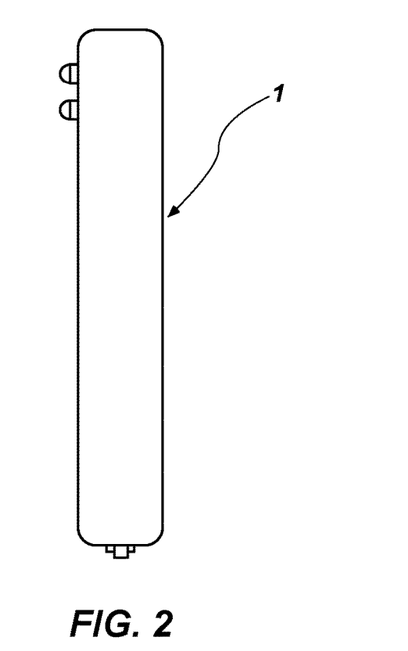
FIG. 2 shows a side view of the data collection box of FIG. 1.

As shown in FIG. 2, some embodiments of the electronic housing 1 can be quite thin—less than 0.25 inches. While some embodiments may be up to one inch thick, it is advantageous if the electronics housing is small enough to be worn comfortably under clothing. The box 1 may be shaped by any means known to one of skill in the art, such as punch, shear, laser cutting, casting, molding or injection molding, etc.

Figure 3:
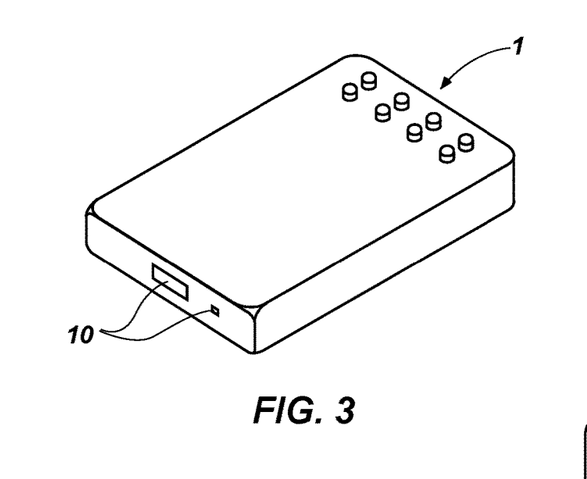
FIG. 3 shows a perspective view of one embodiment of a data collection box.

As shown in FIG. 3, in some embodiments the box 1 may include penetration coverings, gates, or seals 10, which may be pried open or slid aside to access the power button 6, the mode-cycling button (not shown), and/or calibration button (not shown). This feature may reduce the infiltration of water unto the electronics housing unit 1.

Figure 4:
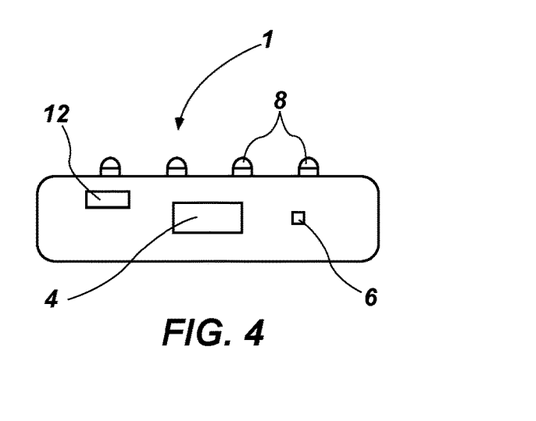
FIG. 4 shows an end view one embodiment of a data collection box.

As shown in FIG. 4, some embodiments may include a USB or connectivity port 4 and accompanying software capable of permitting a firmware upgrade to the gastroesophageal reflux detector and/or a download of information, when the electronics housing is connected to a computer. Additionally, the USB port may be configured to transmit data regarding reflux events automatically when attached to a computer with matching software.

As shown in FIG. 4, the power button 6 may additionally function as a calibration button—for example, when the power button is pressed continuously for a period, such as a period between three and fifteen seconds. A clinician may accordingly calibrate the device manually when placing it on a patient, viewing the results from each sensor via the indicator lights 8, rather than needing to use an external software application to calibrate the detector.

One advantage of the present embodiment is that the electronics housing may be easily attached and removed from a patient—via, for example, a belt clip. This prevents the device from interfering with other medical procedures, such as an MRI or x-ray.

Because only the external surface of the recording unit 1 typically may touch a patient's body, it may easily be wiped down with an alcohol swab, and need not be provided in a sterile condition. Unlike in many other devices for detection of esophageal reflux, no wires are in contact with the patient's body, reducing the risk of shock or damage to the wiring.

In addition, the electronics housing 1 may be equipped with a speaker unit 12, configured to provide audible feedback to a practitioner or user. For example, the speaker unit 12 may produce a tone when a sensor comes loose, or when battery life or storage capacity is low. A user or clinician may wish to accordingly reattach the sensor, recalibrate the device, or take steps necessary to download the recorded data.

Further, the electronics housing 1 may be configured to automatically shut down after a period of time, such as one or three days, or when a pre-programmed number or severity of reflux events is recorded.

Figure 5:
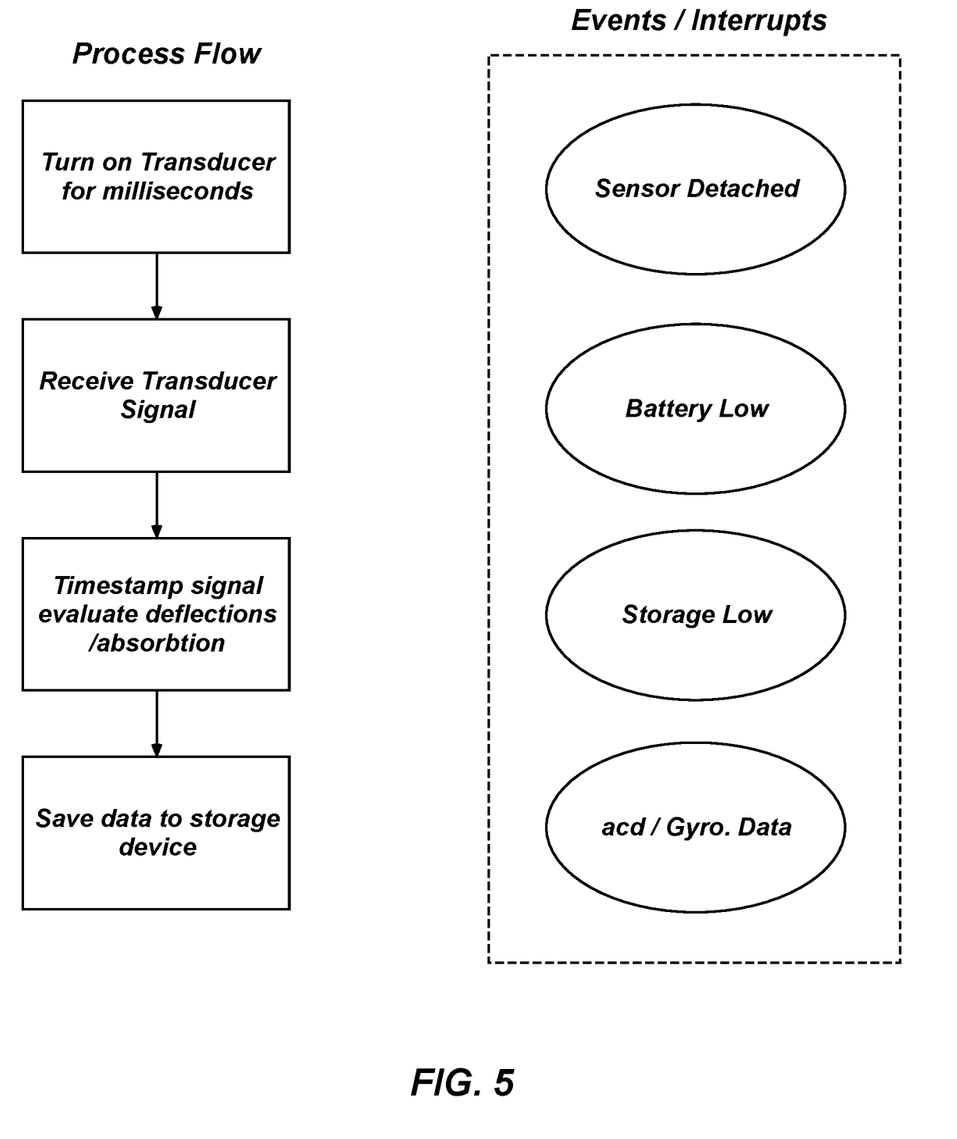
FIG. 5 shows a process flow chart for software running on a data collection box.

Turning now to FIG. 5, there is shown a flowchart of software processes and events or interruptions. During ordinary operation, the pictured embodiment activates one or more transducers for a period of milliseconds. The resulting signal is then received and assigned a timestamp. The ratio of emitted to received signal strength can indicate whether an unwanted event has taken place, such as the detachment of a sensor.

Upon recording the sensor signal data, the process is then repeated. Interruptions to the process may occur if, for example, the battery or storage capacity has become low, or if accelerometer/gyroscopic data (generated by embodiments in which an accelerometer or gyroscope is present) suggest that the recording device or electronics housing (FIGS. 1-4) has been dropped or otherwise violently disturbed.

Figure 9:
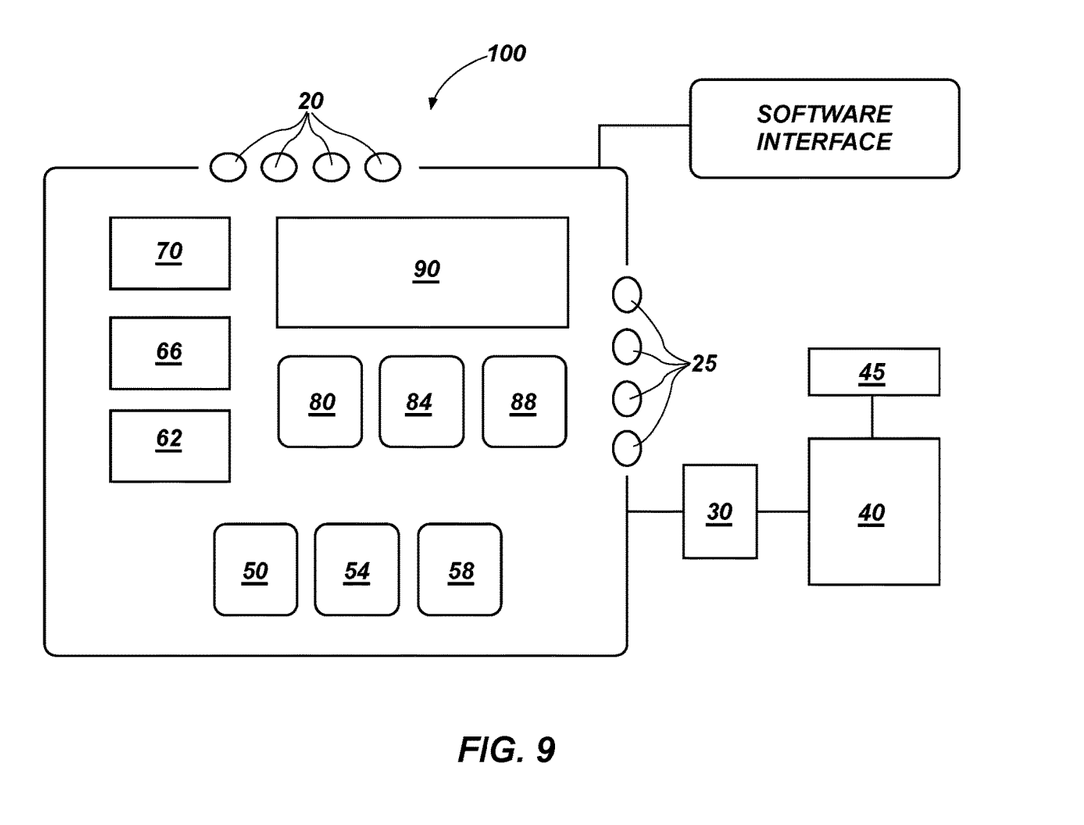
FIG. 9 shows one embodiment of a hardware block diagram for a data collection box.

Turning now to FIG. 9, there is shown a hardware block diagram of one embodiment of components contained within the electronics housing (FIG. 1.) The present embodiment includes utility indicators 20, which may be, for example, a battery indicator, a power plugged in indicator, a data storage indicator, and a device on indicator, or other indicators relevant to the functioning and condition of the gastroesophageal reflux detector.

Sensor indicators 25 are adapted to provide information regarding the functioning of any attached sensors via, for example: adapting lights to dim or blink when a particular sensor is functioning correctly or incorrectly, or the sensor has been placed in a position suitable for discovering useful data. It is advantageous if both utility indicators 20 and sensor indicators 25 are for example bright enough, or loud enough, to provide information that can be discerned easily in daylight or in moderately noisy conditions.

The pictured hardware diagram further includes a power and ground sensor 30, for the detection of electrical shorts or power outages, whether caused by shock, damage, disconnected sensor, or low battery.

The pictured embodiment further includes at least one sensor 40. The sensor 40 may be a grid or panel of several sensors, or several such grids. Additionally, the gastroesophageal reflux detector may include an array of multiple sensors. The sensors may be, for example, a piezoelectric transducer, operating in a range from 100 kHz to 10 MHz. The transducers may be laid out in for example a 10×10 grid, forming squares, strips or diamonds, which may be about 5 inches on a side.

In use, the transducer arrays or sensors 40 are positioned against the skin of the chest and the back, and detect a high frequency sound wave in typically the 100 kHz to 10 MHz range. These low frequency transducers or sensors 40 detect acoustic reflections allowing the esophageal state to be identified by an acoustic signature depending on whether or not the esophagus is open or closed (see detailed discussion below). In some embodiments, electromagnetic waves may be used instead of mechanical sound waves, in which case radio frequency transducers are used in place of the ultrasound transducers, typically in a frequency range between 300 MHz to 300 GHz band.

Sensors 40 may be adapted to provide frequent sampling compared to current technology, for example, sampling up to 100 times a second. The sensors may be selected so that their frequency of sampling may be universally throttled (when battery life or storage capacity is low, for example), or may be selectively throttled. (Some of the individual sensors in a 5-inch by 5-inch grid, for example, may never be in a position over the esophagus unless the grid is peeled off and replaced. These sensors may never produce useful data or a functional signal to noise ratio, and so may be throttled to sample much less frequently in order to conserve battery life and storage space.) Transducers or sensors 40 attached to the small, wearable data acquisition system, may record acoustic signals from the transducers for a period of over 24 hours depending on the needs of the particular patient. Those acoustic signals may then be downloaded and processed by software, such as software that performs pattern recognition on the acoustic signals to detect esophageal state changes at discrete points along the length of the esophagus.

The signals that may captured by the ultrasonic transducers or sensors 40 can be thought of in terms of A-Mode Ultrasound Imaging. In this mode of imaging, at every tissue interface or boundary between two different materials, an acoustic reflection occurs. This reflection or echo is detected by the transducer 40. Boundaries that have a greater impedance mismatch result in a stronger reflection which equates to a stronger current and thus voltage spike in the data. Mapping these echoes against the time of flight (TOF) or the time it takes for the acoustic wave to propagate through the various tissues and return to the transducer as a reflection or echo allows for the generation of an acoustic signal snapshot or frame from that transducer, where the y-axis is the amplitude of the echo, and the x-axis is the TOF. The acoustic signals captured by transducers or sensors 40 are capable of differentiating changes in the diameter and thickness of the esophageal lumen with a resolution of 1 mm.

The acoustic frames are captured from all transducers 40 in the array allowing for the identification of the esophageal state along its length at several transverse planes. These acoustic frames may typically be captured from about 0.1 Hz to about 100 Hz. Frames then undergo signal processing to identify periods of time when an acoustic signature occurs which indicates a bolus-filled esophagus at that transverse plane. The signal processing looks at surrounding frames and focuses on the echoes that fall within a specified TOF which correlates to the depth of the esophagus from the ultrasonic transducer or sensor 40. The signal processing algorithm identifies the tissue layers of the esophagus including the outer and inner walls of the esophageal lumen as well as the distance between these walls. Two key identifiers that indicate the esophagus is expanded is when the strong outer wall echoes have an increase in TOF between them, as well as a concurrent decrease in the TOF of the echoes of the outer and inner esophageal lumen walls. This can be seen in FIG. 6.

Figure 6:
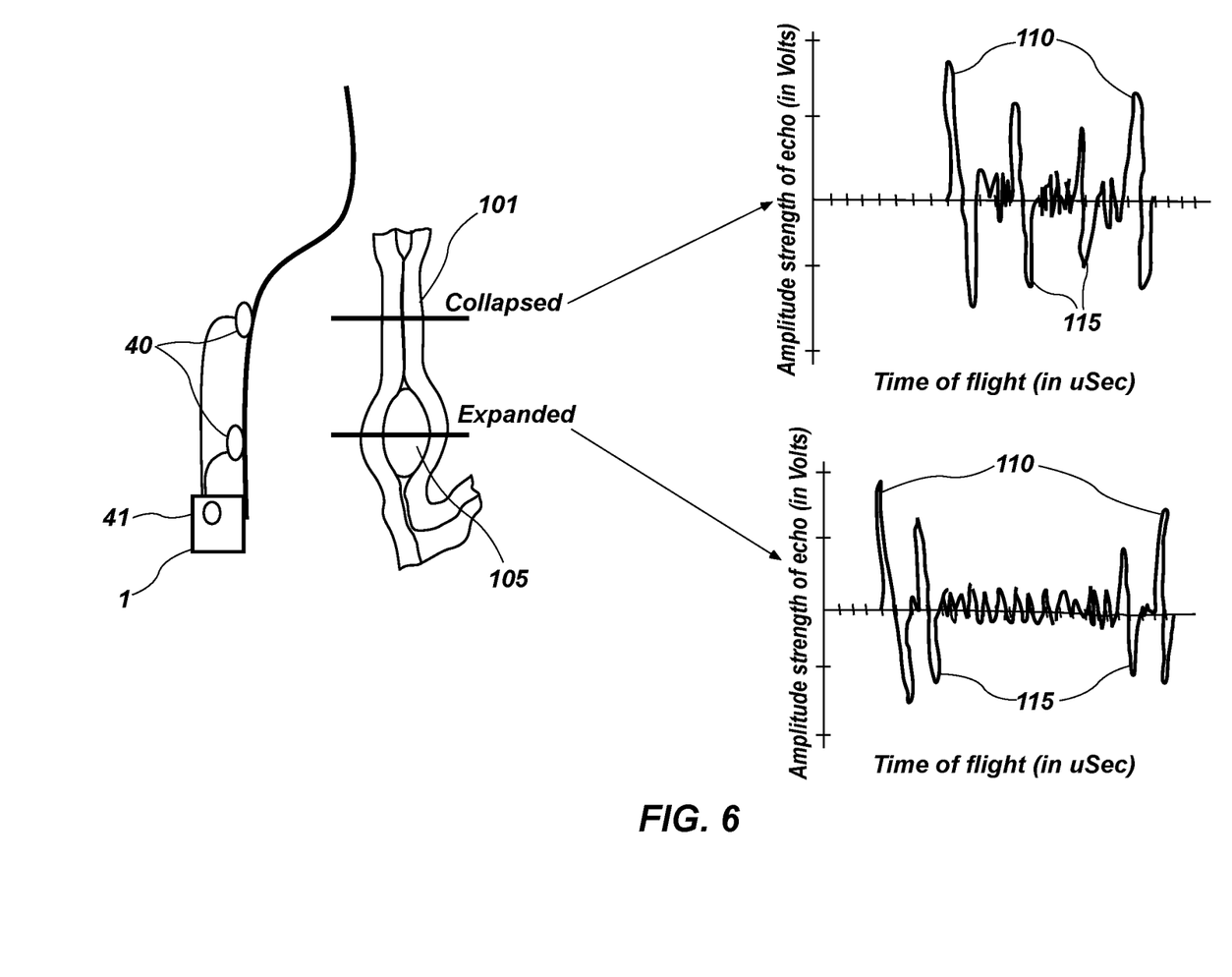
FIG. 6 shows an exemplary bolus in an esophagus with exemplary data outputs received by sensors.

The left side of FIG. 6 shows an esophageal lumen dissected at two transverse planes, one where the esophagus is collapsed 101, and the other where a bolus exists 105, leading to esophageal expansion. The upper right is a representative drawing of the acoustic frame that would characterize a collapsed esophagus 101, with strong echoes 110 depicting the outer walls and smaller echoes 115 being the inner walls. The y-axis is the amplitude strength of the echo (units may vary, for example, and may typically be in microvolts), while x-axis is the TOF (units may vary, for example, and may typically be microseconds). The lower right is a representative drawing of the acoustic frame that would characterize an expanded esophagus 105, and the time between strong outer wall reflections 110 have increased and time between outer wall 110 and inner wall 115 reflections have decreased. The y-axis is echo amplitude and the x-axis is TOF.

Figure 7:
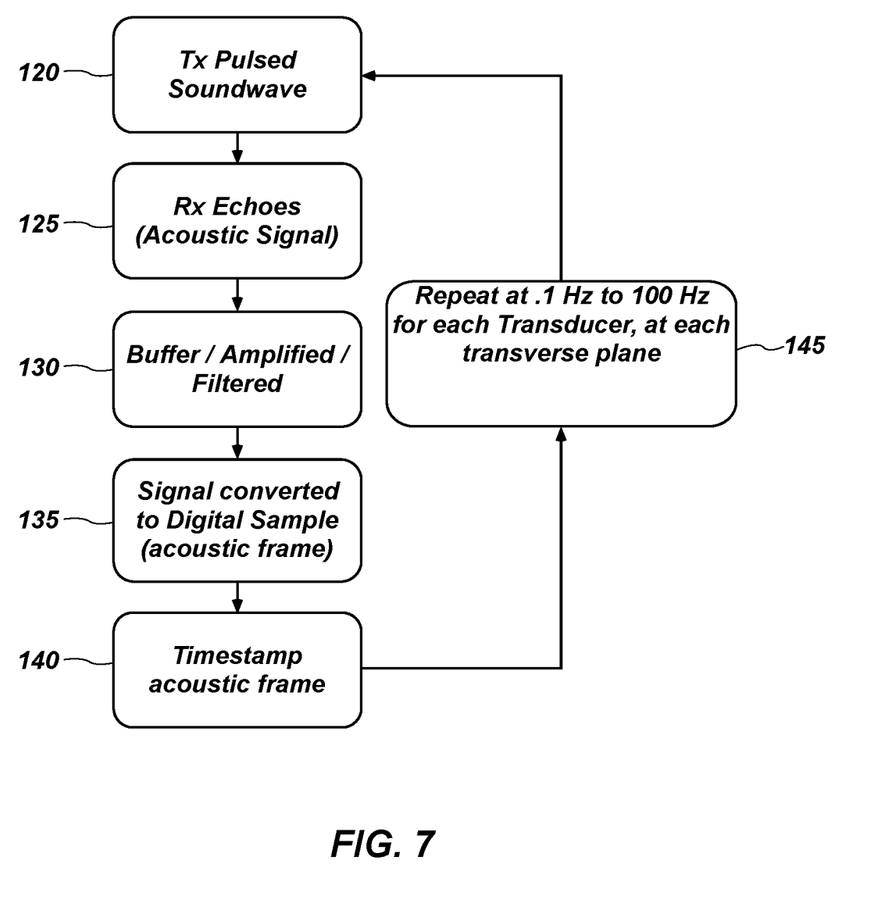
FIG. 7 shows an exemplary process flow chart for a microprocessor to record and store data relating to the acoustic signals detected at each individual transducer.

FIG. 7 illustrates an exemplary flow chart for collecting acoustic data associated with each transducer 40 in the array. It will be appreciated that while the flow charts herein are shown have discrete steps in a particular order, the order may be changed and/or steps may be combined, and substantially the same results may be achieved. Thus the order of the steps is shown by way of example and not of limitation. Turning to FIG. 7, the microprocessor may first send a signal to the transmitter driving circuit (Tx) to output a sound wave pulse on the transducer (120). (It will be appreciated that a transducer may be used, or a transmitter and receiver.)

The transducer then detects any resultant echoes for a predetermined time frame (for example, approximately 200 µs) and records this acoustic signal (125). The acoustic signal may then be buffered, amplified, and filtered by the analog front end or analog front-end controller (130). The acoustic signal may then be digitized, such as with an analog-to-digital convert to form a digital sample or acoustic frame (135). The acoustic frame is a series of discrete coordinates (x, y) where x represents the time of flight (TOF)(such as in µS or nS), and y represents the amplitude in µVolts. Each frame may then be timestamped (140). This process then repeats, for example, at a rate of 0.1 Hz to 100 Hz, on each transducer 40 in the array (145). The process may be repeated for any desired amount of time. For example, 120 hours may produce clinically meaningful data, but more or less time may be recorded as desired.

At the same time the acoustic frames are captured, such as using the method described in FIG. 7, supporting events may also be recorded. For example, positional sensors 41 may be provided and may detect the position of the data collection box. This data may be given a timestamp. Positional sensors 41 may be used to detect and record the time at which a patient changes position, i.e. sits up, lays down, stands up, etc. The positional sensors may be used to detect and record the time when a patient is active or sedentary. Auxiliary sensors 45 may also be used to capture data at discrete points in time. For example, a microphone may be used as an auxiliary sensor to detect and record acoustic events such as a cough, cry, hiccup, chewing, etc.

The frames or time periods that are indicative of a bolus filled esophagus may be recorded/timestamped. When the data is analyzed offline, these periods of an expanded esophagus can be seen at the various transverse planes. Noting the level of the expansion from one plane to the other can dictate directionality of bolus travel, that is, expanded esophagus at proximal end of the array moving distal would indicate a swallow event, while the reverse would be reflux. Examining all acoustic frames that represent an expanded esophagus would aid a clinician in identifying abnormal reflux episodes, or greater than normal amounts of reflux.

Figure 8:
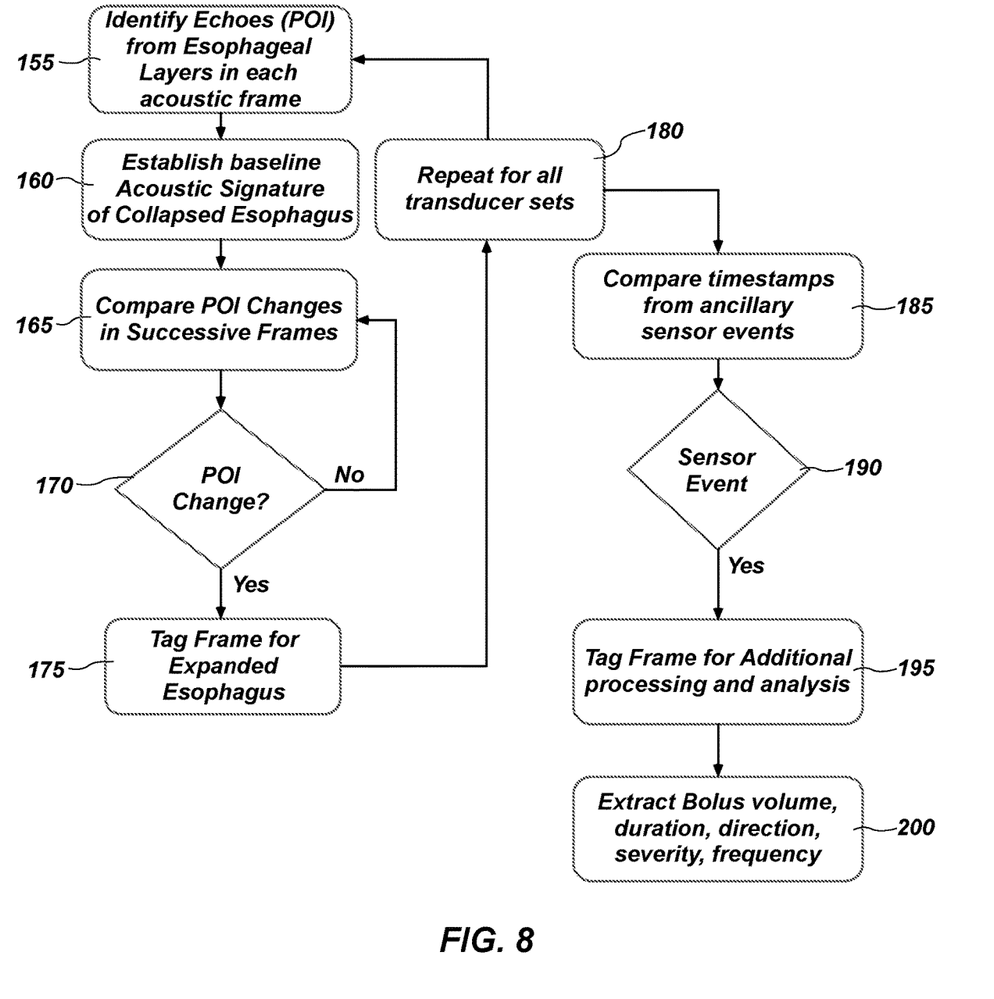
FIG. 8 shows an exemplary process flow chart for processing of the acoustic signals detected at each individual transducer.

FIG. 8 shows an exemplary flow chart for processing acoustic frames. Changes to the acoustic signals from one instant to the next can be thought of as an acoustic signature that identifies the physiological state of the esophagus as either expanded or collapsed. Utilizing multiple single point transducers at various transverse planes and examining the acoustic signature, the state of the esophagus can be monitored to determine the direction of bolus flow, distinguishing between swallow and reflux events.

Turning now to FIG. 8, the acoustic frames (such as acoustic frames collected in the manner shown in FIG. 7) may be combined to create an acoustic data movie. Each acoustic frame in the acoustic data movie contains Points of Interest (POI). For example, in FIG. 6 the strong peaks 110 depicting the outer walls, and smaller echoes 115 depicting the inner walls may each be labeled as a POI. Each POI may represent an echo that correlates to the different layers of the esophagus, such as the outer and inner esophageal wall which have a greater amplitude than other POIs. The processing software may first identify each POI (155). Next, the software may use the POIs to establish a baseline acoustic signature representative of a collapsed or resting esophagus (160). For example, the TOF between POI and their corresponding amplitude may be used to specify the baseline for analyzing the acoustic frames. A frame with POIs that are closer in time may be used to establish the baseline of the collapsed or resting esophagus.

Next, successive frames are analyzed from a single transverse plane (transducer level) to identify changes in POIs to identify the acoustic signature of an expanded esophagus (165). Two changes in POI that may help identify an expanded esophagus are (1) an increase TOF between the outer walls of esophageal lumen, and (2) a decrease in the TOF between the outer and inner walls of the esophageal lumen. These may occur as a result of the volume of the bolus expanding the esophagus, and causing it to stretch, bringing the outer and inner walls closer together. The software may identify an expanded esophagus by any suitable manner. For example, the software may compare the TOF between the outer walls of the esophageal lumen for a particular frame with the TOF between the outer walls of the esophageal lumen established in the baseline. Where the TOF is greater than the baseline, the software may identify this frame as a possible bolus/reflux event. The software may inquire as to whether there is a change in the POIs for each successive acoustic frame (170), and where there is a change, this acoustic frame may be tagged for a possible expanded esophagus event (175). This process of identifying POIs (155), establishing a baseline (160), comparing POI changes from successive frames to identify an expanded state of the esophagus (165), determining if there is a POI change from successive frames (170), and tagging acoustic frames that have a change in POI (175), may be repeated for each transducer 40 of the array (180).

After an expanded state of the esophagus has been identified (175), the processor may use timestamps of supporting events to discriminate and identify a true reflux event or add correlative data points (185). For example, timestamped events recorded from an auxiliary sensor such as a microphone 45 may identify events such as a cough, cry, hiccup, chewing, etc., which are not indicative of a true reflux. Sensor events may be correlated with timestamps of acoustic frames for expanded esophagus events (190). Frames may then be tagged for additional processing and analysis (195). The processor may also extract other data relating to each true reflux (200), such as the bolus volume, duration, direction, severity, frequency, and other data associated with similar time stamps (such as data collected from positional sensors 41 used to detect and record the time at which a patient changes position, i.e. sits up, lays down, stands up, etc.). The bolus volume and duration may be extracted from the acoustic data movie, the direction and severity/height in esophagus that the reflux traveled may be extracted from the acoustic data moving at multiple transverse planes, the frequency of reflux and clearing may be extracted from the number of occurrence over a period of time in the acoustic movie.

Positional sensors 41 may be included to allow for additional correlation of events preceding and during the reflux episode, i.e. laying down for extended periods, or increased activity including walking or running. These correlation events can be added to bolus directionality to aid in determining what might be causing the reflux and what next steps could be taken.

Turning now to FIG. 9, there is shown a block diagram of circuitry that may be used for the esophageal state detector. In addition to sensor(s) 40, and positional sensors 41, an auxiliary or first pass sensor 45 may be used in conjunction with the sensors 40. The auxiliary sensor 45 may be, for example, a microphone. During periods in which a user is eating or drinking, a high volume of sound may be produced. If this sound is detected, the remaining portion of the sensors 40 may be safely and automatically turned off, without danger of missing an otherwise-detectable reflux event (because the user is engaged in swallowing.) Conversely, many people experience high levels of reflux while sleeping, when esophageal sound levels are low. Sensors 40 may be configured to sample more frequently during this period. By including an auxiliary or first pass sensor 45, the detection device may operate more efficiently, conserving battery life and reducing the number of samples that can provide little useful data.

In addition, the pictured embodiment includes an external direct current (DC) connector 50, USB hardware 54, and an SD card reader 58 for expanded data storage capacity. The hardware may additionally include charging circuitry 62, a voltage regulator 66, and a battery pack with battery charge indicator 70. It is advantageous if the battery pack and charge indicator 70 are in a sealed enclosure, and are not readily accessible, in the event the gastroesophageal reflux detector is dropped or broken open.

The esophageal reflux detector may further include a digital signal processor (DSP) or microprocessor 80. A digital signal processor is a specialized microprocessor adapted for processing real-time data, but it will be appreciated that any microprocessor with clock speed and capacity to sufficiently process incoming data from the sensors 40 before storage may be used. A DSP may further distinguish between signals arriving from various sensors, and may be adapted to disregard the signals produced by sensors which do not provide meaningful data, or to throttle the number of samples taken by such sensors, which may have been improperly placed. This selectivity between sensors may conserve both battery life and storage space.

Filters 84 may also be provided. Filters may be, for example, either software or hardware, analog or digital filters. However, providing digital filters 84 may result in better separation of signal from noise or interference, or other signals, particularly when many sensors 40 are placed in close proximity, as with the grid or panel arrangements of sensors 40.

The reflux detector may further include weak signal amplifiers or amplifiers 88, in order to magnify the signals produced by the sensors 40 for better processing. The signal amplifiers 88 may be dynamically adjusted (for example, by the DSP 80) to amplify the output of particular sensors 40 more or less, according to the comparative quality of data they produce. This feedback mechanism reduces the impact of poorly-positioned sensors on any final readouts of potential reflux events, while preserving the usefulness of those sensors if, for example, the sensor panel 40 has become detached and then been replaced.

Figure 10:
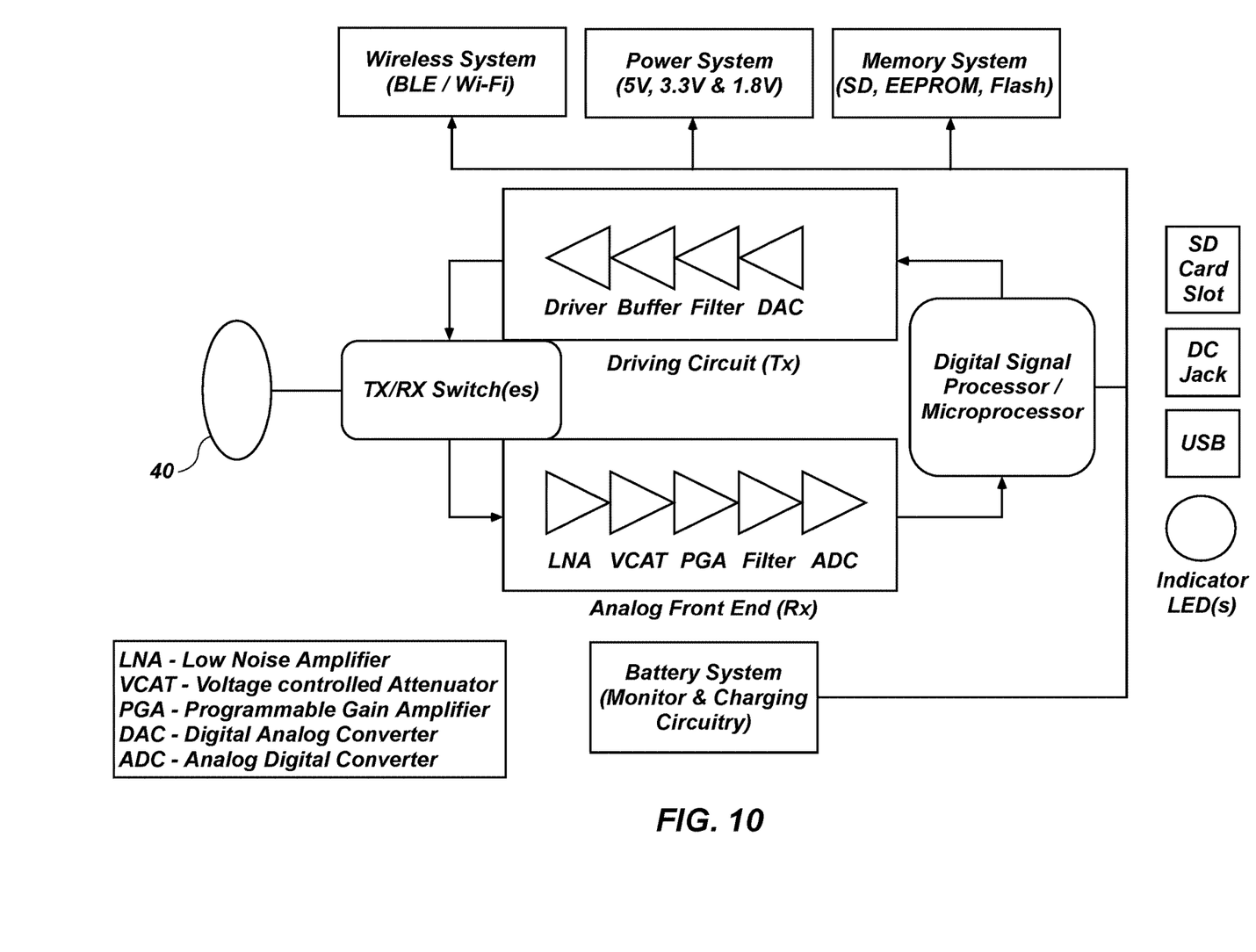
FIG. 10 shows another embodiment of a hardware block diagram for a data collection box.

FIG. 10 shows a more detailed hardware block diagram for electrical components that may be used with the device for detecting an esophageal state.

The reflux detector may further include a microprocessor or digital processor 90, such as a field-programmable gate array (FPGA). It will be appreciated that additional memory units such as FLASH or EEPROM may be included.

Routines included on the microprocessor or digital processor 90 may be, for example, designed to protect patient confidentiality (for example, routines which delete data from the SD card 58 or other storage device if the detector is disassembled or if access is requested by unauthorized users), and may include a real time clock for accurate date stamps of data—an advantage in determining what activities the user was engaging in when the reflux event occurred.

In some situations, the microprocessor or digital processor 90 may be sufficiently capable of post-processing data so that results at a particular level of granularity may be forwarded to another device, such as the user's cellular phone. In such cases, the gastroesophageal characterization device generally indicated at 100 may include a wireless data transfer mechanism, such as Bluetooth®, WiFi hardware, etc.

Additionally, the gastroesophageal characterization device detector generally indicated at 100 may include a software interface capable of downloading and analyzing the data generated by the sensors 40. It may be advantageous if the software allows a clinician to view potential reflux events on varying timescales—that is, to zoom in or out, and examine data sets of varying granularity—and also to allow a clinician to apply different filters in order to sort the data, either manually or automatically.

It is advantageous if the software highlights reflux events as well as correlated airway events (such as burping, or swallowing, which may be determined e.g. by a microphone 45), and is capable of sorting and displaying the data from up to twelve sensors or sensor grids. It is further advantageous if the software allows for determination of the duration of the reflux event, as well as the physical distance any given reflux event travels in the esophageal tract (as measured by the placement of sensors over the esophageal tract, for example, when a grid measuring 5 inches by 5 inches is placed over the esophageal tract).

Figure 11:
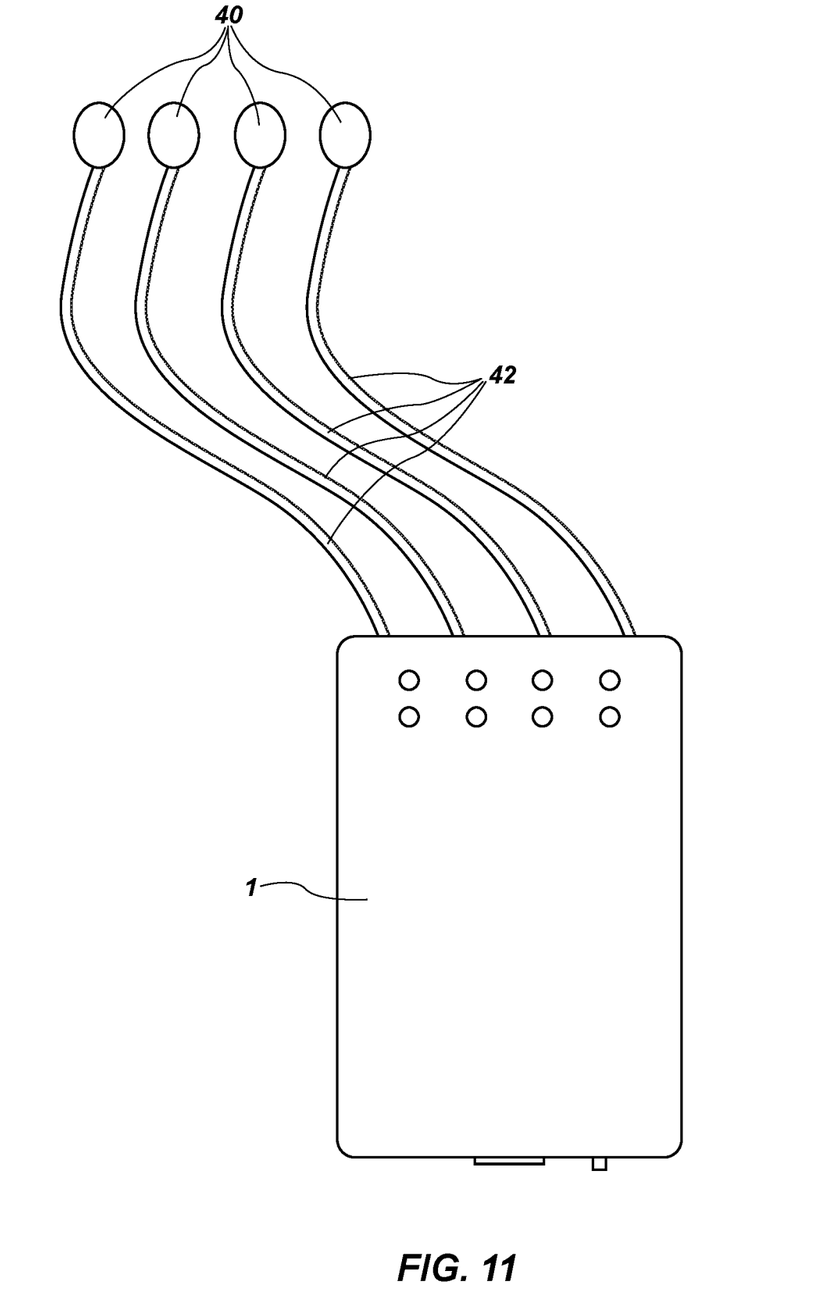
FIG. 11 shows an embodiment of a data collection box connecting to sensing apparatus.

Turning now to FIG. 11, there is shown an embodiment of a data collection box connecting to sensing apparatus. In the present embodiment, the data collection box 1 is connected to four individual sensors 40, however it will be appreciated that the sensors 40 may instead be panels of sensors laid out in a grid, (i.e. a sonography array) or a strip or array of sensors.

The sensors may be disconnectable from either or both the leads 42 or the data collection box 1. Sensors 40 may be contained in environmentally-sealed enclosures or substantially enclosed in a pad, capable of operating over a physiological range of temperature and humidity, and may be compatible with skin contact. Some advantages maintaining an environmentally sealed enclosure for the sensors include reducing signal noise and improving patient comfort. Sensors 40 may be provided sterile, for single use only, and may include an adhesive backing with a peel force not exceeding 1 lb per linear inch.

Sensors 40 connect to the data collection box 1 by means of leads 42. While separate leads 42 are shown, it will be appreciated that leads 42 may instead comprise a single wire bundle (as, for example when the sensors 40 are to be placed very close together, such as when a panel or grid of sensors is used.) Leads may be flexible, thin, and insulated.

It may be advantageous if the entire gastroesophageal characterization assembly, including wires, sensors, and data collection box, weighs under two pounds. Patients wearing sensors or sensor panels 40 report greater comfort when the weight of sensors or sensor panels 40 does not exceed approximately 200 grams, or seven ounces.

Thus there is disclosed a system and method relating to esophageal characterization. It will be appreciated that modifications may be made within the ordinary skill in the art and the appended claims are intended to cover such modifications. For example, the device and method described herein may be used to determine the collapsed or expanded state of not just an esophagus, but also other expanded or collapsed states or volumetric changes of other organs or vessels.

It will be appreciated that various aspects of the present disclosure may be used together. Thus, for example, a system for monitoring and characterizing an esophageal state may include: an ambulatory data collection box having output indicators, the output indicators comprising sensor status indicators and utility indicators; leads in electric communication with the data box; and a sensor pad in electric communication with the leads, the sensor pad comprising at least two sensors. The system may also include at least one of the utility indicators comprising a speaker, the sensors comprising ultrasonic transducers, the ultrasonic transducers being adapted to function in a range between 100 kHz to 10 MHz, the sensors having a sampling frequency, the ambulatory data collection box being adapted to alter the sampling frequency of the sensors simultaneously, the sensors having a sampling frequency, the ambulatory data collection box being adapted to alter the sampling frequency of one sensor independently of other sensors, the data collection box further comprising a battery, a power and ground sensor, a voltage regulator, and a digital processor, and/or the system further comprising a software interface, the software interface comprising granularity selection, and combinations thereof.

Likewise, a method of detecting and characterizing an esophageal state may include: providing the system for detecting an esophageal state according to claim 1; attaching the at least two sensors proximal to an esophagus of a patient; emitting at least one sound wave at each of the at least two sensors; detecting at least one echo resulting from the at least one sound wave at each of the at least two sensors; and recording a time of flight between the at least one sound wave and at least one echo at each of the at least two sensors. The method may further include the step of attaching the at least two sensors proximal to an esophagus of the patient including attaching a first of the at least two sensors in a first transverse plane and a second of the at least two sensors in a second transverse plane, the step of emitting at least one sound wave at each of the at least two sensors including emitting a plurality of sound waves at each of the at least two sensors; the step of detecting at least one echo resulting from the at least one sound wave at each of the at least two sensors comprises detecting a plurality of echoes at each of the at least two sensors; and wherein the step of recording a time of flight between the at least one sound wave and at least one echo at each of the at least two sensors comprises recording the time of flight between each of the plurality of sounds waves and the plurality of echoes at each of the at least two sensors, further comprising the step of: generating an acoustic time frame for each of the at least two sensors representative of the plurality of echoes and time of flight, further comprising the step of identifying at least one point of interest in the acoustic time frame, further comprising the step of analyzing a plurality of points of interest on a plurality of acoustic time frames, further comprising the step of analyzing multiple acoustic frames to determine acoustic frames representative of a collapsed esophagus and an expanded esophagus, and/or further comprising the step of providing an ancillary sensor to record an esophageal event not representative of gastroesophageal reflux, and assigning a time to the esophageal event which is not gastroesophageal reflux, and combinations thereof.

The present disclosure also teaches a system for characterizing esophageal events, the system comprising: a wearable acquisition device comprising a microprocessor; and an array of at least two ultrasonic transducers in electrical connection to the wearable acquisition device. The system may further include the at least two ultrasonic transducers including a first transducer and a second transducer, and wherein the first transducer is configured to be placed proximal to a first transverse plane of an esophagus, and the second transducer is configured to be placed proximal to a second transverse plane of the esophagus. The system may further include the wearable acquisition device further comprises one or more auxiliary sensors and/or one or more auxiliary sensors including at least one of a microphone, an accelerometer, a gyroscope, and a positional sensor.

What is claimed is:

1. A system for monitoring and characterizing an esophageal state of a user's esophagus comprising:
    an ambulatory data collection box comprising a microprocessor and one or more auxiliary sensors, the one or more auxiliary sensors comprising at least one of a microphone, an accelerometer, a gyroscope, and a positional sensor;
    a sensor pad to be placed on the skin of the user near the user's esophagus, the sensor pad in communication with the microprocessor, the sensor pad comprising a first ultrasonic transducer, wherein the first ultrasonic transducer is to be attached to skin of the user in a first transverse plane of the user's esophagus;
    at least one processor programmed to generate a plurality of acoustic frames representative of an amplitude and a time of flight;
    the at least one processor programmed to analyze the plurality of acoustic frames to determine an acoustic frame representative of a baseline esophageal state and measure a first distance between an outer and an inner wall of the user's esophagus;
    the at least one processor programmed to analyze at least a second acoustic frame and measure a second distance between the outer and the inner wall of the user's esophagus; and
    the at least one processor programmed to compare the first distance to the second distance and assign an expanded esophageal state when the second distance is smaller than the first distance.

2. The system of claim 1, further comprising a second ultrasonic transducer, the first ultrasonic transducer and the second ultrasonic transducer having a sampling frequency, the ambulatory data collection box being adapted to alter the sampling frequency of the first ultrasonic transducer and second ultrasonic transducer simultaneously.

3. The system of claim 1, further comprising a second ultrasonic transducer, the first ultrasonic transducer and the second ultrasonic transducer, each having a sampling frequency, the ambulatory data collection box being adapted to alter the sampling frequency of the first ultrasonic transducer independently of the second ultrasonic transducer.

4. The system of claim 1, wherein the ambulatory data collection box further comprises a battery, a power and a ground sensor, a voltage regulator, and a digital processor.

5. The system of claim 1, further comprising a software interface, the software interface comprising a granularity selection.

6. The system of claim 1, wherein the microprocessor is further programmed to identifying at least one point of interest in each of the acoustic frames, and analyze the at least one point of interest in each of the acoustic frames to determine acoustic frames representative of the baseline esophageal state and acoustic frames representative of a change in the baseline esophageal state.

7. The system of claim 6, wherein the one or more auxiliary sensors are configured to record an extra-esophageal event, and wherein the microprocessor is programmed to assign a time to the extra-esophageal event which is not representative of a bolus.

8. The system of claim 1, wherein the microprocessor is further programmed to assign a baseline esophageal state when the second distance equal to the first distance.

9. The system of claim 1, wherein the microprocessor comprises the at least one processor.

10. A system for characterizing esophageal events, the system comprising:
    a wearable acquisition device comprising a microprocessor; and
    at least one ultrasonic transducer, the at least one ultrasonic transducer configured to be placed proximal to a first transverse plane of an esophagus;
    at least one processor programmed to receive acoustic data from the at least one ultrasonic transducer representative of a time of flight and an amplitude;
    the at least one processor programmed to assign a first distance between outer walls of the esophagus based on the acoustic data;
    the at least one processor programmed to assign a second distance between the outer walls of the esophagus based on the acoustic data; and
    the at least one processor programmed to compare the first distance to the second distance and the processor further programmed to assign an expanded esophageal state when the second distance is greater than the first distance.

11. The system according to claim 10, wherein the wearable acquisition device further comprises one or more auxiliary sensors.

12. The system according to claim 11, wherein the one or more auxiliary sensors comprise at least one of a microphone, an accelerometer, a gyroscope, and a positional sensor.

13. The system of claim 12, wherein the at least one processor is programmed to generate an acoustic frame representative of the acoustic data and identify at least one point of interest in the acoustic frame.

14. The system of claim 13, wherein the at least one processor is further programmed to identify and analyze a plurality of points of interest on a plurality of acoustic frames.

15. The system of claim 14, wherein the at least one processor is further programmed to analyze multiple acoustic frames to determine acoustic frames representative of a baseline esophagus state and a change in the baseline esophagus state.

16. The system of claim 10, wherein the microprocessor comprises the at least one processor.

17. A method of detecting and characterizing an esophageal state of an esophagus of a user, the method comprising:
    attaching a first ultrasonic transducer to a skin of the user proximal to the esophagus;
    generating, by the first ultrasonic transducer, a frequency;
    sensing, by the first ultrasonic transducer, acoustic signals representative of a plurality of amplitudes and times of flight for a first time period and a second time period;
    generating, by a processor, a first acoustic frame representative of the plurality of amplitudes and the times of flight for the first time period, and a second acoustic frame representative of the plurality of amplitudes and the times of flight for the second time period;

determining a first maximum amplitude in the first acoustic frame;

determining a second maximum amplitude in the second acoustic frame; and assigning an expanded state of the esophagus when the second maximum amplitude is greater than the first maximum amplitude.

18. The method according to claim 17, further comprising the step of providing an ancillary sensor to record an esophageal event not representative of a bolus, and assigning a time to the esophageal event which is not a bolus.

* * * * *